(12) United States Patent
Collins et al.

(10) Patent No.: US 6,303,036 B1
(45) Date of Patent: Oct. 16, 2001

(54) METHOD AND APPARATUS FOR EFFICIENT HEMODIAFILTRATION

(75) Inventors: Gregory R. Collins, Monroe; Edward C. Spence, Bronx, both of NY (US)

(73) Assignee: Nephros, Inc., New York, NY (US)

( * ) Notice: Subject to any disclaimer, the term of this patent is extended or adjusted under 35 U.S.C. 154(b) by 0 days.

(21) Appl. No.: 09/485,778

(22) PCT Filed: Jul. 30, 1999

(86) PCT No.: PCT/US99/17468

§ 371 Date: Mar. 1, 2000

§ 102(e) Date: Mar. 1, 2000

(87) PCT Pub. No.: WO00/06292

PCT Pub. Date: Feb. 10, 2000

Related U.S. Application Data

(60) Provisional application No. 60/094,898, filed on Jul. 31, 1998.

(51) Int. Cl.[7] ............... B01D 61/24; B01D 61/28; B01D 61/32; B01D 63/00
(52) U.S. Cl. ............... 210/646; 210/143; 210/252; 210/321.6; 210/321.72; 210/323.1; 210/416.1; 210/645; 210/650; 210/929
(58) Field of Search ............... 210/252, 434, 210/321.6, 87, 321.72, 90, 323.1, 97, 645, 646, 929, 143, 650, 739, 416.1; 604/4.01, 5.04

(56) References Cited

U.S. PATENT DOCUMENTS

| | | |
|---|---|---|
| 3,579,441 | 5/1971 | Brown . |
| 3,878,095 | 4/1975 | Frasier et al. ............... 210/87 |
| 3,946,731 | 3/1976 | Lichtenstein ............... 128/214 |
| 4,038,190 | 7/1977 | Baudet et al. ............... 210/321 |
| 4,118,314 | 10/1978 | Yoshida ............... 210/22 |
| 4,381,999 | 5/1983 | Boucher et al. ............... 210/637 |
| 4,498,990 | 2/1985 | Shaldon et al. ............... 210/637 |
| 4,647,378 | 3/1987 | Minami ............... 210/646 |
| 4,702,829 | 10/1987 | Polaschegg et al. ............... 210/195.2 |
| 4,708,802 | 11/1987 | Rath et al. ............... 210/641 |
| 4,722,798 | 2/1988 | Goss et al. ............... 210/646 |
| 4,770,769 | 9/1988 | Schael ............... 210/96.2 |
| 4,784,495 | 11/1988 | Jonsson et al. ............... 366/151 |
| 4,834,888 | 5/1989 | Polaschegg ............... 210/646 |
| 4,861,485 | 8/1989 | Fecondini ............... 210/641 |
| 5,011,607 | 4/1991 | Shinzato ............... 210/637 |
| 5,069,788 | 12/1991 | Radovich et al. ............... 210/321.8 |
| 5,075,003 | 12/1991 | Aoyagi ............... 210/321.8 |

(List continued on next page.)

FOREIGN PATENT DOCUMENTS

| | | |
|---|---|---|
| 0076422 | 4/1983 | (EP) . |
| 0 516 152 A1 | 12/1992 | (EP) . |
| 0 960 624 A2 | 12/1999 | (EP) . |
| WO 98 30258 | 7/1998 | (WO) . |
| WO 98/35710 | 8/1998 | (WO) . |

OTHER PUBLICATIONS

Canaud et al., Artificial Organs 11(2): 18–190 (1987).

(List continued on next page.)

Primary Examiner—John Kim
(74) Attorney, Agent, or Firm—Darby & Darby

(57) ABSTRACT

An apparatus and method for hemodiafiltration are disclosed. The apparatus includes a first dialyzer cartridge containing a semi-permeable membrane that divides the dialyzer into a blood compartment and a dialysate compartment. Fluid discharged from the blood compartment of the first dialyzer cartridge is mixed with sterile substitution fluid to form a fluid mixture and the mixture enters a second dialyzer cartridge. The second dialyzer cartridge contains a second semi-permeable membrane which divides the second dialyzer cartridge into a blood compartment and a dialysate compartment. Hemodiafiltration occurs in both cartridges.

20 Claims, 2 Drawing Sheets

U.S. PATENT DOCUMENTS

| | | | |
|---|---|---|---|
| 5,178,763 | 1/1993 | Delaunay | 210/644 |
| 5,194,157 | 3/1993 | Ghezzi et al. | 210/646 |
| 5,244,568 | 9/1993 | Lindsay et al. | 218/87 |
| 5,318,750 | 6/1994 | Lascombes | 422/81 |
| 5,431,811 | 7/1995 | Tusini et al. | 210/90 |
| 5,476,592 | 12/1995 | Simard | 210/651 |
| 5,487,827 | 1/1996 | Peterson et al. | 210/87 |
| 5,511,875 | 4/1996 | Jonsson et al. | 366/136 |
| 5,660,722 | 8/1997 | Nederlof | 210/90 |
| 5,690,831 | 11/1997 | Kenley et al. | 210/646 |
| 5,702,597 | 12/1997 | Chevallet et al. | 210/195 |
| 5,711,883 | 1/1998 | Folden et al. | 210/646 |
| 5,725,775 | 3/1998 | Bene et al. | 210/646 |
| 5,725,776 | 3/1998 | Kenley et al. | 210/646 |
| 5,744,042 | 4/1998 | Stange et al. | 210/645 |
| 5,808,181 | 9/1998 | Wamsiedler et al. | 73/38 |
| 5,846,419 | 12/1998 | Nederlof | 210/323.1 |
| 5,882,516 | 3/1999 | Gross et al. | 210/321.6 |

OTHER PUBLICATIONS

Sato et al., Artificial Organs 22(4): 285–290 (1998).

Technical Aspects of High–Flux Hemodiafiltration for Adequate Short (Under 2 Hours) Treatment (pp. 377–380)(undated).

Hemodiafiltration with On–Line Production of Substitution Fluid: Long–Term Safety and Quantitative Assessment of Efficacy, Contrib Nephrol. Basel, Karger, 1994, vol. 108, pp. 12–21.

Albertini, B. von et al.: High–Flux Hemodiafiltration: Under Six Hours/Week Treatment. vol. XXX Trans Am Soc Artif Intern Organs 1984, pp. 227–230.

Albertini, B. von et al.: Performance Characteristics of High–Flux Hemodiafiltration. Abstract from $2^{nd}$ Annual Workshop of the International Society of Hemofiltration. Blood Purification 2:44–64 (1984).

Fremont et al.: Evaluation of Short–Time Hemofiltration. Abstract from $2^{nd}$ Annual Workshop of the International Society of Hemofiltration. Blood Purification 2:44–64 (1984).

Ghezzi, P.M. et al.: Hemodiafiltration Without Replacement Fluid ASAIO Journal 1992.

Ghezzi, P.M et al.: Use of the ultrafiltrate obtained in two–chamber (PFD) hemodiafiltration as replacement fluid. The International Journal of Artificial Organs/vol. 14/No. 6, 1991/pp. 327–334.

Ghezzi, P.M. et al.: Extracorporeal Blood Purification in Uremic Patients by a Separate Convective–Diffusive System. Abstract from $2^{nd}$ Annual Workshop of the International Society of Hemofiltration. Blood Purification 2:44–64 (1984).

Kim, Sung–Teh: Characteristics of Protein removal in Hemodifiltration. Maeda K. Shinzato T (eds): Effective Hemodiafiltration:New Methods. Contrib Nephrol. Baser, Karger, 1994, vol. 108, pp. 23–37.

Marangoni, Roberto et al.: Short Time Treatment with High–Efficiency Paired Filtration Dialysis for Chronic Renal Failure. Artificial Organs 16 (6):547–552, Blackwell Scientific Publications, Inc., Boston 1992 International Society for Artificial Organs.

Ono, Masataka et al.: Comparison of Types of On–Line Hemodiafiltration from the Standpoint of Low–Molecular––Weight Protein Removal. Maeda K. Shinzato T (eds): Effective Hemodiafiltration:New Methods. Contrib Nephrol. Baser, Karger, 1994, vol. 108, pp. 38–45.

Polaschegg, Hans–Dietrich et al.: Hemodialysis Machines and Monitors, Hemofiltration and hemodiafiltration pp. 354–356 (undated).

Ronco, C. et al.: Technical and Clinical Evaluation of Different Short, Highly Efficient Dialysis Techniques. Contr. Nephrol., vo. 61, pp. 46–68 (Karger, Basel 1988).

Ronco, C. et al.: Comparison of four different short dialysis techniques. The International Journal of Artificial Organs/vol. 11/No. 3, 1988/pp. 169–174.

Ronco, C. et al.: Paired Filtration Dialysis: Studies of Efficiency, Flow Dynamics and Hydraulic Properties of the System. Blood Purif 1990; 8:126–140.

Rotellar, Emilio et al.: Large–Surface Hemodialysis. Artificial Organs 10(5):387–396, Raven Press, New York, 1986 International Society for Artificial Organs.

Sanz–Moreno, C. et al.: Hemodiafiltration in Two Chambers Without Replacement Fluid: A Clinical Study. Artificial Organs 19(5):407–410 Blackwell Scientific Publications, Inc., Boston 1995 International Society for Artificial Organs.

Shaldon, S. et al.: Mixed Hemofiltration (MHF): 18 Months Experience With Ultrashort Treatment Time. vol. XXVII Trans Am Soc Artif Intern Organs 1981, pp. 610–612.

Shinaberger, James H. et al.: 16: Short Treatment, Techniques for shortened treatment pp. 372–375.

Sternby, Jan: A Decade of Experience with On–Line Hemofiltration/Hemodiafiltration. Maeda K. Shinzato T (eds): Effective Hemodiafiltration:New Methods. Contrib Nephrol. Baser, Karger, 1994, vol. 108, pp. 1–11.

Vanholder et al.: In vivo solute elimination of paired filtration dialysis. The International Journal of Artificial Organs/vol. 14/No. 1, 1991/pp. 23–27.

Zucchelli, P. et al.: Paired Filtration Dialysis: Optimizing Depurative Efficiency with Separate Convection and Diffusion Processes. Nephron 1990; 56:166–173.

Shinzato et al.: Infusion–Free Hemodiafiltration: Simultaneous Hemofiltration and Dialysis with No Need for Infusion Fluid. Artificial Organs 1982; 6: 453–456.

METHOD AND APPARATUS FOR EFFICIENT HEMODIAFILTRATION

This application claims benefit of Provisional Application Ser. No. 60/094,898 filed Jul. 31, 1998.

FIELD OF THE INVENTION

The present invention relates to a blood cleansing modality known as hemodiafiltration.

BACKGROUND OF THE INVENTION

Hemodiafiltration combines standard dialysis and hemofiltration into one process, whereby a dialyzer cartridge containing a high flux membrane is used to remove substances from the blood both by diffusion and by convection. The removal of substances by diffusion is accomplished by establishing a concentration gradient across a semipermeable membrane by flowing a dialysate solution on one side of the membrane while simultaneously flowing blood on the opposite side of the membrane. To enhance removal of substances using hemodiafiltration, a substitution fluid is continuously added to the blood either prior to the dialyzer cartridge (pre-dilution) or after the dialyzer cartridge (post-dilution). An amount equal to that of the substitution fluid is then ultrafiltered across the dialyzer cartridge membrane carrying with it additional solutes.

Substitution fluid is usually purchased as a sterile/non-pyrogenic fluid contained in large flexible bags or is produced by on-line by filtration of a non-sterile dialysate through a suitable filter cartridge rendering it sterile and non-pyrogenic. Such on-line production of substitution fluid is described, inter alia, in D. Limido et al., "*Clinical Evaluation of AK-100 ULTRA for Predilution HF with On-Line Prepared Bicarbonate Substitution Fluid. Comparison with HD and Acetate Postdilution HF*", International Journal of Artificial Organs, Vol. 20, No.3 (1997), pp. 153–157.

In general, hemodiafiltration schemes use a single dialyzer cartridge containing a high flux semi-permeable membrane. Such a scheme is described, for example, in P. Ahrenholz et al., "*On-Line Hemodiafiltration with Pre- and Postdilution: A comparison of Efficiency*", International Journal of Artificial Organs, Vol. 20, No.2 (1997), pp 81–90 ("Ahrenholz et al."). Substitution fluid is introduced into the blood stream either in a pre-dilution mode or in a post-dilution mode relative to the dialyzer cartridge. The preferred mode for maximal removal of both small and large substances from blood is the post-dilution mode, which achieves the highest concentration gradient between the blood and the dialysate fluid. In a typical pre-dilution mode with on-line generation of the substitution fluid, however, the bloodside concentration is lowered relative to the dialysate fluid. As a result, removal (or clearance) of substances can decrease, as described in Ahrenholz et al. This is particularly true for smaller molecules like urea, whereby mass transport is driven more by the diffusion process than by the convection process.

A hemodiafiltration scheme using first and second dialyzer cartridges is described in J. H. Miller et al., "Technical Aspects of High-Flux Hemodiafiltration for Adequate Short (Under 2 Hours) Treatment", Transactions of American Society of Artificial Internal Organs (1984), pp. 377–380. In this scheme, the substitution fluid is reverse-filtered through a membrane of the second dialyzer cartridge with simultaneous filtration of fluid across a membrane in the first dialyzer cartridge. Counter-current flow of dialysate occurs at both cartridges.

Certain trade-offs exist with respect to removal of different size molecules when comparing pre-dilution diafiltration and post-dilution diafiltration using a single dialyzer cartridge. For example, with on-line pre-dilution diafiltration, one can achieve higher convective filtration rates (compared to on-line post-dilution diafiltration) to enhance removal of large molecules, however, this comes at the expense of reducing the removal of small molecules like urea and creatinine. In on-line post-dilution diafiltration, however, only a limited amount of fluid can be filtered from the blood as it passes through the dialyzer cartridge. The filterable amount is dependent upon several factors, including blood flow rate, blood hematocrit and blood protein concentration. Typically, the filterable amount is 20% to 30% of the incoming blood flow, depending on blood flow rate. For example, at a blood flow rate of 300 ml/min, the filterable amount is limited to about 90 ml/min.

SUMMARY OF THE INVENTION

It is an object of the present invention to provide a hemodiafiltration method and a device which overcome the limitations associated with convection filtration in existing on-line post-dilution schemes. It is also an object of the present invention to reduce the loss of small molecule clearance associated with on-line pre-dilution diafiltration using a single dialyzer cartridge.

The present invention provides an improved method of performing hemodiafiltration. The present invention also provides a device adapted to be used in conjunction with a standard UF controlled dialysis machine, to perform improved hemodiafiltration.

A hemodiafiltration device in accordance with an embodiment of the present invention, adapted for use in conjunction with a dialysis machine, includes a plurality of dialyzers (e.g., dialyzer cartridges or dialyzer cartridge sections) for diafiltration, at least one sterility filter arrangement (e.g., a sterility filter cartridge) for generating a sterile substitution fluid, and a control unit which controls fluid inputs and outputs between the dialyzers, the at least one sterility filter cartridge and the dialysis machine.

The dialyzers may contain a semi-permeable membrane which may be embedded within a jacket or housing of a dialyzer cartridge. The membranes separate each dialyzer into a blood compartment and a dialysate compartment. In an embodiment of the present invention, at least first and second dialyzers are used to carry out the diafiltration process. The at least one sterility filter may also contain semi-permeable membranes. The sterility filter may be used to remove bacteria, endotoxins, and other particulate from the dialysate, thereby to generate a suitable substitution fluid stream on-line. The control unit may contain various pumps, pressure monitoring devices, valves, electronic components, connector fittings, tubing, etc., as required in order to coordinate the operation of the other system components.

Blood enters the bloodside compartment of the first dialyzer, whereby some plasma water is filtered across the semi-permeable membrane into the adjacent dialysate compartment. As the blood leaves the first dialyzer, substitution fluid is added to the blood at a rate higher than the rate at which blood is filtered out of the first dialyzer. The diluted blood then enters the bloodside compartment of the second dialyzer, whereby additional plasma water (equal to the excess amount of substitution fluid) is filtered across the semi-permeable membrane and into the adjacent dialysate compartment. In this manner, the substitution fluid acts as a post-dilution fluid relative to the first dialyzer as well as a pre-dilution fluid relative to the second dialyzer.

An advantage of this process is that a gain in clearance of small molecular weight substances in the first dialyzer overshadows a loss in clearance of small molecular weight substances due to the dilution of blood concentration entering the second dialyzer. Further, clearance of larger molecular weight substances is enhanced considerably, because the total filtration level of plasma water is practically doubled (e.g. 40% to 60% of the incoming blood flow rate may be filtered) compared to filtration using a single dialyzer operating in a post-dilution mode.

BRIEF DESCRIPTION OF THE DRAWINGS

The present invention will be understood and appreciated more fully from the following detailed description of preferred embodiments of the invention, taken in conjunction with the following drawings in which.

DETAILED DESCRIPTION OF PREFERRED EMBODIMENTS

Figure 1:
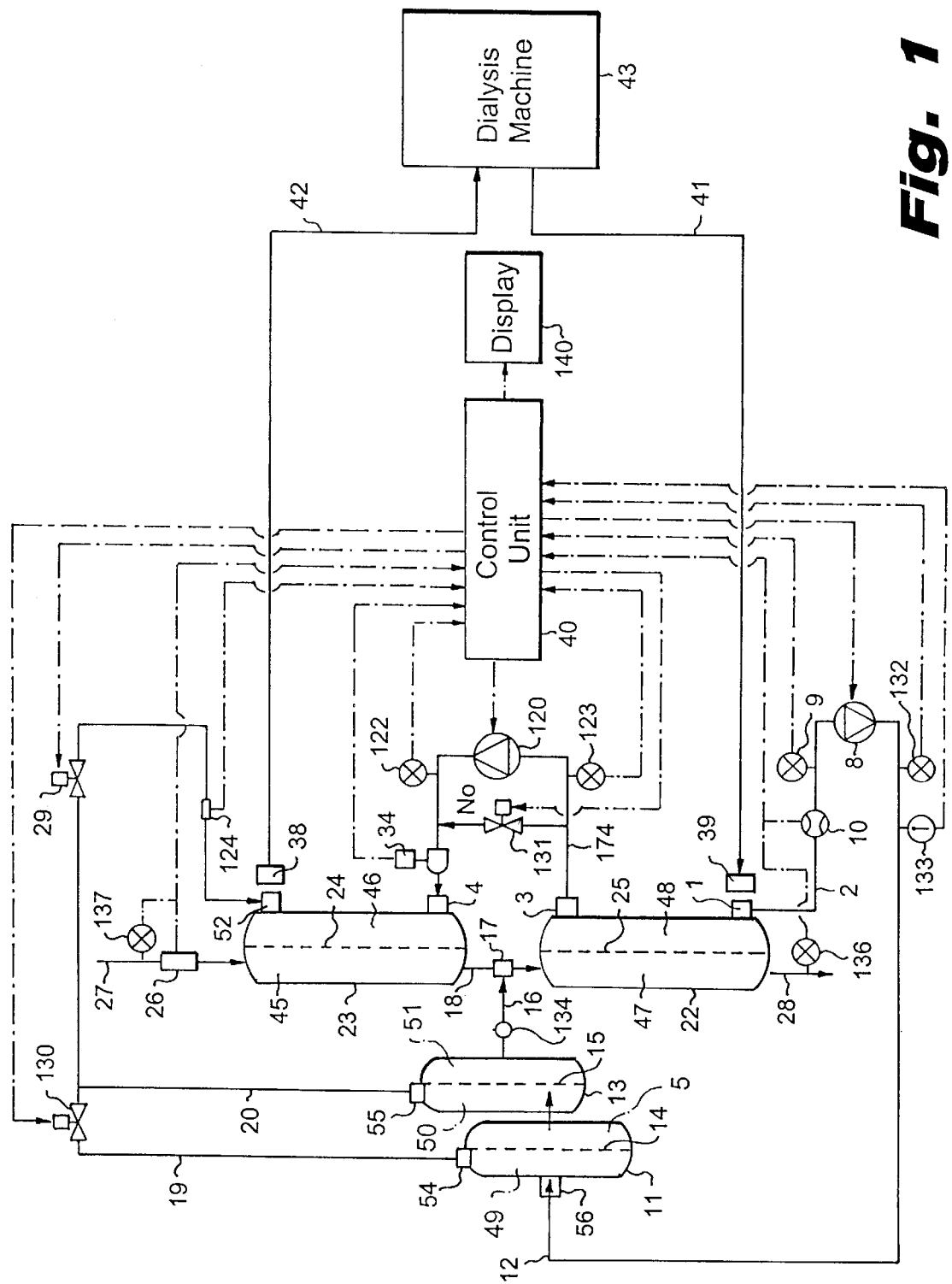
FIG. 1. is a schematic illustration of a dialysis system hemodiafiltration device in accordance with the present invention, used in conjunction with a UF controlled dialysis machine, wherein monitoring of dialyzer transmembrane pressure (TMP) is performed by the dialysis machine.

The hemodiafiltration method and device of present invention will be described below in the context of an add-on type system used in conjunction with an existing UF controlled dialysis machine. It should be appreciated, however, that the hemodiafiltration method and device of the present invention can also be embodied in a stand-alone dialysis/hemodiafiltration machine.

In an embodiment of the present invention, as described below with reference to the drawings, the hemodiafiltration device includes first and second dialyzer cartridges. Alternatively, a single cartridge having at first and second, separate, dialyzer sections may be used. The device also includes at least one sterility filter, which may contain semi-permeable membranes. The sterility is operative to remove bacteria, endotoxins, and other particulate from the dialysate, thereby to generate a suitable substitution fluid stream on-line. The hemodiafiltration device also includes a fluid module to coordinate between different elements of the system. The fluid module contains various pumps, pressure monitoring devices, valves, electronic components, connector fittings, tubing, etc., as required in order to coordinate the operation of the other system components.

During operation of the system, blood enters the bloodside compartment of the first dialyzer cartridge, whereby a portion of plasma water is filtered across the semi-permeable membrane into the adjacent dialysate compartment. As the blood leaves the first dialyzer cartridge, substitution fluid is added to the blood at a rate higher than the rate at which blood is filtered out of the first dialyzer cartridge. The diluted blood then enters the bloodside compartment of the second dialyzer cartridge, whereby additional plasma water (equal to the excess amount of substitution fluid) is filtered across the semi-permeable membrane and into the adjacent dialysate compartment. In this manner, the substitution fluid acts as a post-dilution fluid relative to the first dialyzer cartridge as well as a pre-dilution fluid relative to the second dialyzer cartridge.

It will be appreciated by persons skilled in the art that the process of the present invention provides a considerable gain in clearance of small molecular weight substances in the first dialyzer cartridge, which gain overshadows a loss in clearance of small molecular weight substances due to dilution of blood concentration as the blood enters the second dialyzer cartridge. Further, clearance of larger molecular weight substances is enhanced considerably, because the total filtration level of plasma water is increased considerably (e.g. 40to 60% of the incoming blood flow rate may be filtered) compared to filtration using a single dialyzer cartridge operating in a post-dilution mode.

The dialysate fluid may be generated by the dialysis machine. In an embodiment of the present invention, the dialysate fluid enters the second dialyzer cartridge and runs counter-parallel to the blood flow direction. The dialysate fluid acts to provide a concentration gradient against the bloodside fluid thereby facilitating the diffusion of solutes across the semi-permeable membrane. As the dialysate traverses through the dialysate compartment, the dialysate flow rate increases due to plasma water filtering across into the dialysate compartment as mentioned above.

Upon exiting the second dialyzer cartridge, the dialysate fluid may be pumped into the first dialyzer cartridge, again running counter-parallel to the bloodside fluid. The dialysate flow rate increases as it traverses through the dialysate compartment again, due to filtration of plasma water across the semi-permeable membrane. Upon exiting the dialyzer cartridges, the used dialysate is transported back to the dialysis machine.

The dialysate pump placed between the two dialyzer cartridges serves to regulate the amount of plasma water that is filtered across the membranes of the respective cartridges. For example, increasing the speed of the pump increases the filtration rate in the second dialyzer cartridge while reducing the filtration rate in the first dialyzer cartridge, whereas slowing the speed of the pump reduces the filtration rate in the second dialyzer cartridge while increasing the filtration rate in the first dialyzer cartridge.

A sterile/non-pyrogenic substitution fluid for use in conjunction with the present invention may be prepared by drawing a portion of fresh dialysate solution from the dialysate inlet line and pumping it through a sterile filter cartridge. In an embodiment of the present invention, the sterile filter cartridge performs at least a double filtration of the dialysate solution before the solution is introduced into the blood stream as a substitution fluid. This double filtration can be performed by two separate ultrafiltration filter cartridges or a single cartridge that has multiple sections to perform multiple filtration of the substitution fluid. The use of multiple filtration to generate the on-line substitution fluid makes the system of the present invention safer, should one of the filters fail during treatment.

The dialysis machine used in conjunction with the present invention may perform all of its normal functions, such as preparing dialysate, metering dialysate flow rate, monitoring pressures, controlling net ultrafiltration, monitoring used dialysate for blood presence, etc. The diafiltration add-on system operates in conjunction with the dialysis machine, whereby the dialysate fluid from the dialysis machine is re-distributed by the hemodiafiltration add-on system to its respective dialyzer and sterile filter cartridges. The fluid handling components of the diafiltration add-on system may be integrated with a microprocessor unit for controlling and executing the diafiltration aspect of the treatment.

In one embodiment of the add-on system of the present invention, as described below with reference to FIG. 1, the dialysis machine monitors the transmembrane pressure (TMP) in one of the dialyzer cartridges. The choice of which dialyzer cartridge is monitored may depend on the type of dialysis machine. For example, some existing machines determine TMP based on dialysate inlet pressure, while other existing machines use dialysate outlet pressure as the parameter for TMP calculation. Therefore, in this embodiment of the present invention, the hemodiafiltration add-on system may contain hardware and/or software to ensure that the TMP that is monitored by the dialysis machine is of the cartridge having the worst (i.e., highest) TMP.

In another embodiment of the add-on system of the present invention, as described below with reference to FIG. 2, the dialysate pressure of each dialyzer cartridge may be separately controlled using dialysate pumps on both the inlet and outlet lines of the dialysate. In this arrangement, the dialysate pressures monitored by the dialysis machine may be maintained constant by adjusting the speeds of the inlet and outlet dialysate pumps. Further, in this arrangement, the TMP may be continuously monitored and displayed on one or more of the dialyzer cartridges. Additionally, in some embodiments of the present invention, TMP thresholds may be set to activate different modes, for example, the hemodiafiltration add-on system may be designed to return to a normal dialysis session or to reduce the level of diafiltration once a predetermined TMP threshold is exceeded.

Figure 2:
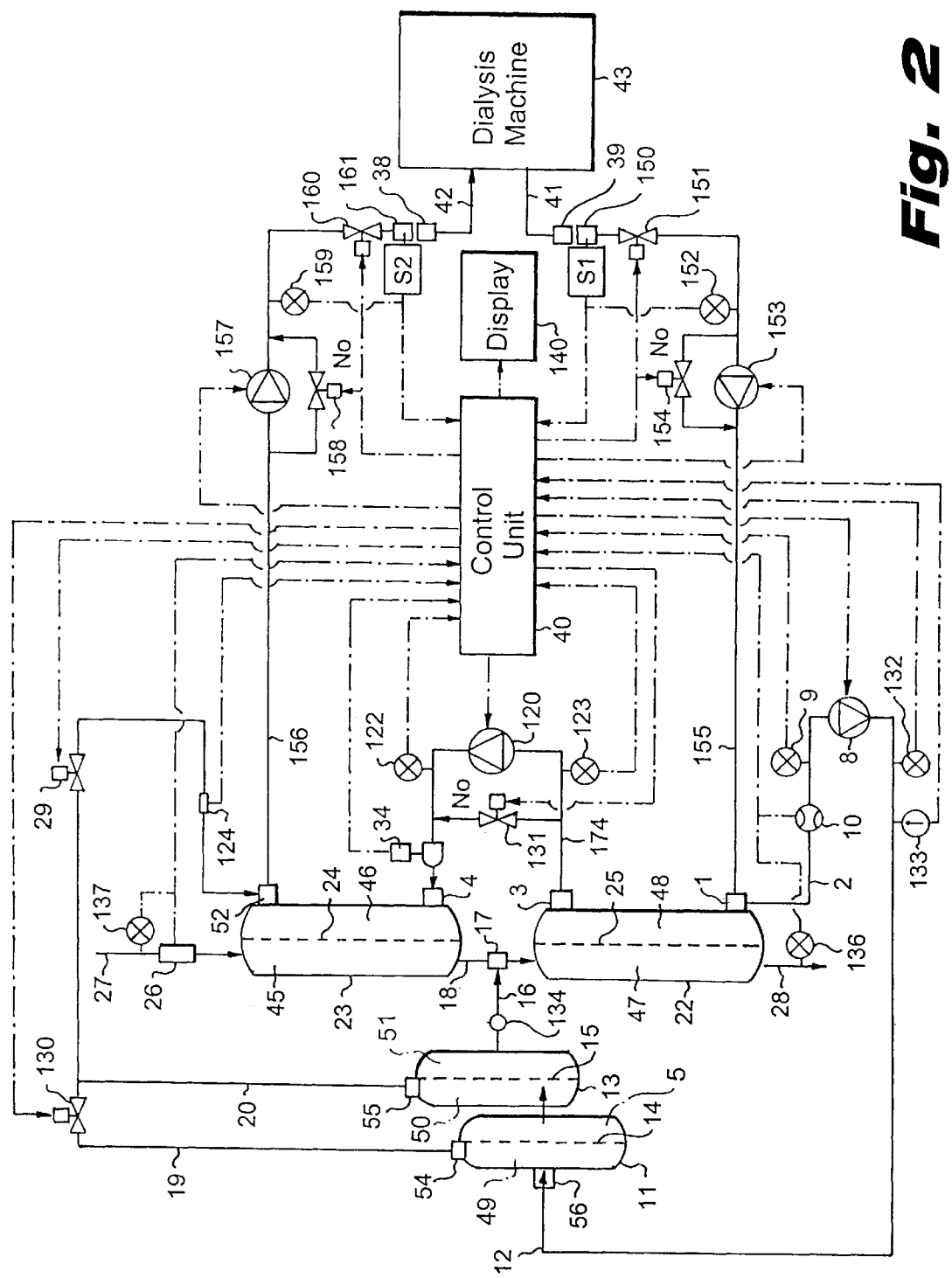
FIG. 2 is a schematic illustration of a second embodiment of a hemodiafiltration device in accordance with the present invention, used in conjunction with a standard UF controlled dialysis machine, wherein dialyzer TMP is monitored by the hemodiafiltration device.

Reference is now made to made to FIGS. 1 and 2 which schematically illustrate two alternative embodiments of a system using a hemodiafiltration device in accordance with an embodiment of the present invention. In both the systems of FIGS. 1 and 2, blood to be cleaned 27 enters a first dialyzer cartridge 23 after passing through blood monitoring devices 137 and 26. Blood monitoring devices 137 and 26 monitor the incoming blood pressure and/or the incoming blood flow rate and provide an input, responsive to the monitored rate, to a control unit 40. The blood is carried by suitable tubing, as is known in the art, for example, bloodline tubing made from flexible polyvinylchloride (PVC). The flow rate of incoming blood is generally in the range of 100 to 600 ml/min, preferably 200 to 500 ml/min.

First dialyzer cartridge 23 contains a semi-permeable membrane 24 that divides the dialyzer into a blood compartment 45 and a dialysate compartment 46. As blood 27 passes through blood compartment 45, plasma water containing blood substances is filtered across semi-permeable membrane 24. Additional blood substances are also transferred across semi-permeable membrane 24 by diffusion due to a difference in concentration between blood compartment 45 and dialysate compartment 46.

The dialyzer cartridge may be of any type suitable for hemodialysis, hemodiafiltration, hemofiltration, or hemoconcentration, for example, the Fresenius F60, available from Fresenius Medical Care, Lexington, Mass. the Baxter CT 110, available from Baxter Health Care, Deerfield, Ill. the Minntech Hemocor HPH 1000, available from Minntech Corporation, Minneapolis, Minn. or the Hospal Filtral 16, available from Hospal A.G., Switzerland. Membrane 24 is preferably a medium to high flux membrane, for example, the polysulfone, cellulose triacetate or acrylonitrile membranes available from Fresenius Medical Care, Lexington, Mass. Minntech Corporation, Minneapolis, Minn. Baxter Health Care, Deerfield, Ill. or Hospal A.G., Switzerland.

Partially dialyzed blood (denoted 18) exiting dialyzer cartridge 23 is mixed with sterile substitution fluid 16 to form a blood/substitution fluid mixture 17. This mixture enters a second dialyzer cartridge 22 containing a semi-permeable membrane 25 which divides the dialyzer cartridge 22 into a blood compartment 47 and a dialysate compartment 48. As mixture 17 passes through blood compartment 47, plasma water containing blood substances is filtered across the semi-permeable membrane. As in the first dialyzer cartridge, additional blood substances are transferred across semi-permeable permeable membrane 25 by diffusion due to concentration gradients between the blood and dialysate compartments. Cleansed blood 28 exits second dialyzer cartridge 22 and is recycled to the patient (not shown) through suitable tubing, for example, bloodline PVC tubing, as is known in the art. The pressure of cleansed blood 28 may also be monitored by a pressure sensor 136.

The second dialyzer cartridge may be of any type suitable for hemodialysis, hemodiafiltration, hemofiltration, or hemoconcentration, for example, the Fresenius F60, available from Fresenius Medical Care, Lexington, Mass. the Baxter CT 110, available from Baxter Health Care, Deerfield, Ill. the Minntech Hemocor HPH 400, available from Minntech Corporation, Minneapolis, Minn. or the Hospal Filtral 16, available from Hospal A.G., Switzerland. Membrane 25 is preferably a medium or high flux membrane, for example, the polysulfone, cellulose triacetate or acrylonitrile membranes mentioned above with reference to membrane 24.

As mentioned above, the dialysate solution used for the present invention may be prepared by a standard UF controlled dialysis machine 43. Fresh dialysate solution flows from dialysis machine 43 through a conduit 41 to a dialysate line connector 39. In a first embodiment of the hemodiafiltration device, shown in FIG. 1, the dialysate line connector 39 is attached to a dialysate inlet port 1 on dialyzer cartridge 22.

In a second embodiment of the hemodiafiltration device, shown in Fig.2, the dialysate line connector 39 is attached to a connector 150 which operates to activate a switch S1 upon connection of line connector 39. With the switch SI activated, a valve 151 is opened to allow flow, via a suitable conduit, to a dialysate pump 153. The pressure en route to pump 153 may be monitored by a pressure transducer 152 upstream of pump 153. A bypass loop containing a valve 154 enables fluid to bypass pump 153 when valve 151 is opened. Fluid from dialysate pump 153 flows through a conduit 155 which is connected to dialysate inlet port 1 on dialyzer cartridge 22.

In an embodiment of the present invention, preparation of a sterile substitution fluid is performed by filtration of a dialysate across at least two filter membranes with a molecular weight cut-off of not more than 40,000 Daltons. To accomplish this, a portion of the fresh dialysate solution may be split off the dialysate fluid stream at some point prior to entering dialysate compartment 48 of the second dialyzer cartridge 22. The split-off portion of the dialysate solution may flow through a conduit 2 leading to a substitution pump 8. Flow rate and pre-pump pressure in conduit 2 may be monitored by a flow meter 10 and a pressure transducer 9. Substitution fluid pump 8 generates the needed pressure to force the fluid down a conduit 12, across first and second sterile filter cartridges, 11 and 13, respectively, and into blood stream 18. En route to sterile filters 11 and 13, post-pump pressure and temperature may be monitored by a pressure transducer 132 and a temperature sensor 133.

First sterile filter cartridge 11 contains a semi-permeable membrane 14 that separates the filter cartridge into an upstream compartment 49 and a downstream compartment 5. Upstream compartment 49 has an inlet port 56 and an outlet port 54, the latter being connected to a conduit 19. Air may be vented from upstream compartment 49, via outlet port 54 and conduit 19 upon opening of a valves 130 and a valve 29. Closing of valve 130 forces the dialysate fluid to filter (or permeate) across semipermeable membrane 14 and into downstream compartment 5.

The filtrate from downstream compartment 5 then flows into second sterile filter cartridge 13 containing a semipermeable membrane 15 which separates the filter cartridge into an upstream compartment 50 and a downstream compartment 51. Upstream compartment 50 has an outlet port 55 for venting air from both compartment 5 of cartridge 11 and compartment 50 of cartridge 13. Outlet port 55 is connected to a conduit 20 which is connected to the venting line between valves 130 and 29. Closing of both valves 29 and 130 forces the dialysate to filter across semi-permeable membrane 15 and into downstream compartment 51. The filtered dialysate flows out of compartment 51 and through a check valve 134, which minimizes blood back-flow into sterile filter cartridge 13.

The sterile dialysate (or substitution fluid) 16 exiting sterile filter cartridge 13 is mixed with blood exiting cartridge 23 to form the blood/substitution fluid mixture 17 described above. In some embodiments of the present invention (not shown in the drawings), a portion of substitution fluid may be added to the blood stream exiting second dialyzer cartridge 22, provided that the blood does not become overly viscous in the second dialyzer cartridge due to hemoconcentration.

During priming or flushing of sterile filter cartridges 11 and 13, valves 130 and 29 are opened to allow flow therethrough. The flow downstream of valve 29 is directed, via a suitable fluid conduit, to a junction near a dialysate outlet port 52 of dialyzer cartridge 23. An air detector 124 may be placed downstream of valve 29, providing an input to control unit 40 to ensure hat that air is purged from sterile filter cartridges 11 and 13 during priming.

The dialysate not used as substitution fluid enters the second dialyzer cartridge 22 through inlet port 1 of dialysate compartment 48, and flows counter-parallel to the blood flow as it traverses through compartment 48. During diafiltration, plasma water filters across semi-permeable membrane 25 and mixes with the dialysate fluid. The dialysate fluid together with the filtered plasma water exits the dialyzer cartridge, at outlet port 3, through a tubing conduit 174 which directs the fluid to a first path, including a bypass valve 131, and a second path including a pump 120. Downstream of valve 131 and pump 120, the two paths are rejoined and the combined fluid flow is connected to an inlet port 4 of dialysate compartment 46 of first dialyzer cartridge 23. Pressure transducers 123 and 122 monitor pre-pumping and post-pumping pressures, respectively, across pump 120, and inputs responsive to these pressures are provided to control unit 40. A flow switch 34 may be placed on the line leading to dialysate inlet port 4, to ensure that a minimum dialysate flow is maintained to carry out the diafiltration operation.

During normal operation of the system, valve 131 is closed whereby all flow is diverted to pump 120. In this mode, the speed of the pump can be used to control the amount of ultrafiltration that occurs across the second dialyzer cartridge membrane 25. For example, if the rate of fluid flow pumped by pump 120 matches the inlet dialysate flow rate into compartment 48, then the net ultrafiltration of fluid across the membrane is zero. Increasing the speed of the pump to pump above the inlet dialysate flow rate results in an ultrafiltration rate equal to the difference between these two flow rates. Dialysate fluid entering first dialyzer cartridge 23 through inlet port 4 runs counter-parallel to the blood flow as it traverses through the dialysate compartment 46. Plasma water filters across semi-permeable membrane 24 of cartridge 23 into compartment 46, where the plasma water is combined with the dialysate fluid, and the combined fluid exits at dialysate outlet port 52.

The used dialysate fluid may be returned to the dialysis machine as follows. In the embodiment of FIG. 1, the dialysis machine dialysate outlet line connector 38 is connected to dialysate outlet port 52. A conduit 42 carries the spent dialysate from the dialysate outlet connector back to dialysis machine 43.

In the embodiment of FIG. 2, used dialysate flows through conduit 156 leading to a dialysate outlet pump 157, having a bypass loop thereacross, similar to the bypass loop described above with reference to dialysate pump 153. The bypass loop of pump 157 includes a valve 158. When valve 158 is opened, dialysate fluid bypasses pump 157. A pressure transducer 159 may be provided downstream of pump 157 to monitor the dialysate pressure of the fluid returning to the dialysis machine. When valve 158 is closed, the speed of the pump can be used to control the dialysate fluid return pressure. The return of fluid to the dialysis machine may be enabled only when connector 161 is properly connected to the dialysis machine connector 38. This can be accomplished by a switch S2, which is activated upon proper connection of connectors 161 and 38, to open a return valve 160.

Control unit 40 includes a processor which controls the diafiltration device. Control unit receives input from various components of the hemodiafiltration device, e.g., pressure transducers, flow meters, flow switches, etc., as described above. Using suitable control hardware and/or software, control unit 40 controls various system functions, such as setting values for pump speeds, opening/closing valves. System parameters may be displayed on a display 140 associated with control unit 40.

What is claimed is:

1. In a blood dialysis system including a source of substitution fluid and a blood dialysis machine, a hemodiafiltration device comprising:
    a first dialyzer including:
        a first membrane;
        said first membrane defining a first blood compartment having a first blood inlet which receives blood and a first blood outlet which discharges partially diafiltered blood; and
        said first membrane defining a first dialysate compartment having a first dialysate inlet and a first dialysate outlet;
    means for mixing said partially diafiltered blood with a substitution fluid to obtain a blood/substitution fluid mixture;
    a second dialyzer including:
        a second membrane;
        said second membrane defining a second blood compartment having a second blood inlet which receives said blood/substitution fluid mixture and a second blood outlet which discharges diafiltered blood; and
        said second membrane defining a second dialysate compartment having a second dialysate inlet and a second dialysate outlet;
    at least one sterility filter which receives dialysate from said dialysis machine and provides sterilized dialysate fluid to said means for mixing; and a control unit which controls the flow of blood through said first and second dialyzers and the circulation of dialysate fluid between the dialysis machine, said first and second dialysate compartments and said at least one sterility filter.

2. A hemodiafiltration device according to claim 1, wherein said first and second dialyzers comprise first and second dialyzer cartridges, respectively, wherein the first membrane in the first dialyzer cartridge is a semi-permeable membrane between said first blood compartment and said first dialysate compartment, and wherein the second membrane in the second dialyzer cartridge is a semi-permeable membrane between said second blood compartment and said second dialysate compartment.

3. A hemodiafiltration device according to claim 1, wherein dialysate fluid is delivered through a first conduit from said dialysis machine to said second dialysate inlet of said second dialyzer where it flows through said second dialysate compartment and exits through a second conduit which connects said second dialysate outlet to said first dialysate inlet, the dialysate fluid flowing through said first dialysate compartment to said first dialysate outlet.

4. A hemodiafiltration device according to claim 1, wherein a first stream of dialysate fluid flows from said dialysis machine through a first conduit to said second dialysate inlet, a portion of said first stream being diverted through a second conduit to said at least one sterility filter.

5. A hemodiafiltration device according to claim 1, wherein said at least sterility filter comprises a first sterility filter and a second sterility filter, said first sterility filter containing a third semi-permeable membrane partitioning said first sterility filter into a first upstream compartment and a first downstream compartment, said second sterility filter containing a fourth semi-permeable membrane partitioning said second sterility filter into a second upstream compartment and a second downstream compartment.

6. A hemodiafiltration device according to claim 5, wherein said dialysate fluid flows through a first conduit to said first upstream compartment from said dialysis machine, said dialysate fluid being filtered across said third semi-permeable membrane before flowing into said second upstream compartment through a second conduit connecting said first and second sterility filters, said dialysate fluid being filtered across said fourth semi-permeable membrane, said second downstream compartment being fluidly connected with said means for mixing by a third conduit so that said sterilized dialysate fluid is introduced thereto.

7. A method of hemodiafiltration comprising the steps of:
supplying a blood inflow;
diafiltering said blood inflow to provide a partially diafiltered blood outflow;
mixing said partially diafiltered blood outflow with a substitution fluid to provide a blood/substitution fluid mixture; and
diafiltering said blood/substitution fluid mixture.

8. A method according to claim 7 wherein the step of diafiltering said blood inflow comprises the step of diffusing a portion of said blood inflow by a first countercurrent of a dialysate solution in diffusion communication with said blood inflow, and wherein the step of diafiltering said blood/substitution fluid mixture comprises the step of diffusing a portion of said blood/substitution fluid mixture by a second countercurrent of the dialysate solution in diffusion communication with said blood/substitution fluid mixture.

9. A method according to claim 8 and further comprising the step of sterilizing said dialysate solution.

10. A method according to claim 8, wherein said substitution fluid is formed by diverting a portion of said dialysate solution to at least one sterilizing filter which sterilizes said dialysate solution to form said substitution fluid.

11. A method according to claim 8, further comprising the step of controlling the flow of blood in said diafiltration steps and circulation of said dialysate fluid using a controller.

12. A method according to claim 7, wherein said blood is diafiltered in a first dialyzer and said blood/substitution fluid mixture is diafiltered in a second dialyzer, said substitution fluid being added and mixed between said diafiltration steps.

13. A method according to claim 12, further comprising the steps of disposing an interstage pump between said first and second dialyzers and adjustably setting a flow rate of the dialysate fluid from said second dialyzer to said first dialyzer at a predetermined rate by manipulating said interstage pump, said dialysate fluid flowing through a conduit from said second dialyzer to said first dialyzer.

14. A hemodiafiltration device comprising:
a source of substitution fluid;
a first dialyzer including:
a first membrane;
said first membrane defining a first blood compartment having a first inlet which receives blood and a first outlet which discharges partially diafiltered blood;
said first membrane defining a first dialysate compartment having a first dialysate inlet for receiving dialysate fluid and a first dialysate outlet;
means for mixing said partially diafiltered blood with said substitution fluid to form a blood/substitution fluid mixture; and
a second dialyzer including:
a second membrane;
said second membrane defining a second blood compartment having a second inlet which receives said blood/substitution fluid mixture and a second outlet which discharges diafiltered blood; and
said second membrane defining a second dialysate compartment having a second dialysate inlet for receiving dialysate fluid and a second dialysate outlet.

15. A hemodiafiltration device according to claim 14, wherein said substitution fluid comprises a portion of said dialysate fluid which flows through a first conduit from a source of dialysate fluid to at least one sterility filter where said portion of said dialysate fluid is sterilized by passing through said at least one sterility filter to form said substitution fluid.

16. A hemodiafiltration device according to claim 15, wherein said first conduit is connected to a dialysis machine which provides dialysate fluid to said at least one sterility filter through said first conduit, said dialysis machine being connected to said second dialysate inlet by a second conduit so that a portion of said dialysate fluid is provided to said second dialysate compartment from said dialysis machine.

17. A hemodiafiltration device according to claim 14, further including:
a control unit operatively connected to said first and second dialyzers for controlling the flow of blood through said first and second dialyzers and the circulation of dialysate fluid through said first and second dialyzers.

18. A hemodiafiltration device according to claim 14, further including:
a dialysis machine for producing dialysate fluid, said dialysis machine being in fluid communication with said second dialysate compartment by a first conduit, a second conduit extending between said second dialysate outlet and said first dialysate inlet permitting said dialysate fluid to flow from the second dialysate compartment to the first dialysate compartment of said first and second dialyzers.

19. A hemodiafiltration device according to claim 14, further including:

an interstage pump disposed between said first and second dialyzers and in fluid communication with said first and second dialysate compartments, said interstage pump being controllable so that a flow rate of the dialysate fluid from said second dialyzer to said first dialyzer is adjustably set at a predetermined rate.

20. A hemodiafiltration device comprising:

a source of substitution fluid;

a first dialyzer including:

a first membrane defining a first blood compartment and a first dialysate compartment;

said first blood compartment having a first inlet which receives blood and a first outlet which discharges blood having a first concentration of toxins;

said first dialysate compartment having a first dialysate inlet for receiving dialysate fluid and a first dialysate outlet;

means for mixing said blood having said first concentration of toxins with said substitution fluid to form a blood/substitution fluid mixture; and a second dialyzer including:

a second membrane defining a second blood compartment and a second dialysate compartment;

said second blood compartment having a second inlet which receives said blood/substitution fluid mixture and a second outlet which discharges blood having a second concentration of toxins, the first concentration of toxins being greater than the second concentration of toxins; and said second dialysate compartment having a second dialysate inlet for receiving dialysate fluid and a second dialysate outlet.

* * * * *